(12) United States Patent
Leskosek

(10) Patent No.: US 9,771,383 B2
(45) Date of Patent: Sep. 26, 2017

(54) MODIFIED OPIOIDS CONTAINING SILICON

(71) Applicant: James Andrew Leskosek, Summerland (CA)

(72) Inventor: James Andrew Leskosek, Summerland (CA)

( * ) Notice: Subject to any disclaimer, the term of this patent is extended or adjusted under 35 U.S.C. 154(b) by 0 days.

(21) Appl. No.: 14/710,777

(22) Filed: May 13, 2015

(65) Prior Publication Data

US 2016/0362430 A1    Dec. 15, 2016

Related U.S. Application Data

(60) Provisional application No. 61/992,647, filed on May 13, 2014.

(51) Int. Cl.
| | |
|---|---|
| *C07F 7/10* | (2006.01) |
| *C01B 21/092* | (2006.01) |
| *A61K 31/695* | (2006.01) |
| *C07F 7/18* | (2006.01) |
| *C07F 7/21* | (2006.01) |
| *C07F 7/08* | (2006.01) |

(52) U.S. Cl.
CPC .............. *C07F 7/10* (2013.01); *A61K 31/695* (2013.01); *C01B 21/092* (2013.01); *C07F 7/0801* (2013.01); *C07F 7/1844* (2013.01); *C07F 7/1856* (2013.01); *C07F 7/1868* (2013.01); *C07F 7/1872* (2013.01); *C07F 7/21* (2013.01)

(58) Field of Classification Search
CPC ........ C07F 7/10; C07F 7/1868; C07F 7/1872; C07F 7/0801; C01B 21/092
USPC .......................................................... 544/1
See application file for complete search history.

(56) References Cited

PUBLICATIONS

Search Report dated Feb. 17, 2016, in respect of corresponding GB Patent application No. GB1508154.0.

Kenji Uchida, Satoshi Yokoshima, Toshiyuki Kan & Tohru Fukuyama, Total Synthesis of Morphine, Organic Letters Journal, Oct. 10, 2006, pp. 5311-5313, vol. 8 No. 3, American Chemical Society.

Chih-Hung Wu et al., Evaluation of various derivatization approaches for gas chromatography—mass spectrometry analysis of buprenorphine and norbuprenorphine, Journal of Chromatography A, 2008, pp. 93-112, vol. 1182 (1), Elsevier B.V., Taiwan.

Teemu Gunnar et al., Validated toxicological determination of 30 drugs of abuse as optimized derivatives in oral fluid by long column fast gas chromatography/electron impact mass spectrometry, Journal of Mass Spectrometry, 2005, pp. 739-753, vol. 40(6), John Wiley & Sons Limited online.

National Institute of Standards and Technology Mass Spectral Library Database, (entered STN: Sep. 3, 2008) see compound having the molecular formula C25 H37 NO3 Si3 and the CAS Registry No. 1046143-85-4.

National Institute of Standards and Technology Mass Spectral Library Database, (entered STN: Aug. 3, 2008) see compound having the molecular formula C25 H41 NO3 Si3 and the CAS Registry No. 1037839-99-8.

National Institute of Standards and Technology Mass Spectral Library Database, (entered STN: Jul. 31, 2008) see compound having the molecular formula C23 H37 NO3 Si2 and the CAS Registry No. 1037511-85-5.

National Institute of Standards and Technology Mass Spectral Library Database, (entered STN: Jul. 18, 2008) see compound having the molecular formula C23 H35 NO3 Si2 and the CAS Registry No. 1034619-31-2.

Jerzy Lukasiak et al., Absorption and distribution of orally administered siloxanes in rat organs, Polimery 2001, 46, nr 7-8, pp. 546-548.

*Primary Examiner* — Kahsay Habte

(74) *Attorney, Agent, or Firm* — Antony C. Edwards

(57) ABSTRACT

A modified opioid is provided comprising modified morphine molecules, wherein for each morphine molecule, one or more carbon atoms are replaced with silicon atoms. A method is further provided for modifying an opioid comprising morphine molecules, said method comprising the step of replacing one or more carbon atoms with silicon atoms.

13 Claims, 11 Drawing Sheets

MODIFIED OPIOIDS CONTAINING SILICON

FIELD OF THE INVENTION

The present invention relates to modified opioids containing silicon.

BACKGROUND OF THE INVENTION

Opioids are psychoactive molecules that resemble morphine or similar molecules in their pharmacological effects. The primary therapeutic use of opioids is to produce an analgesic effect, otherwise referred to as a painkiller effect, whereby the perception of pain is decreased and the tolerance of pain is increased. Opioids are amongst the world's oldest known drugs, with examples of the morphine molecule being extracted from poppy flowers found in recorded history. Morphine, one of the most commonly known opioids, has the chemical formula C17H19NO3 and its molecular structure is well known.

Opioids operate on humans by binding to opioid receptors, which are primarily located in the central and peripheral nervous system and the gastrointestinal tract. Today, the primary clinical use of opioids is the treatment of severe pain such as post-operative pain. Although opioids are amongst the best known drugs for effective relief of severe pain, there are many undesirable side effects of opioids, which side effects include sedation, respiratory depression, constipation, nausea and vomiting, and addiction to the sense of euphoria it may induce. That is, ongoing administration of opioids may result in opioid dependence, leading to withdrawal symptoms upon abrupt discontinuation of opioids. Opioid dependence may also result in the need to increase the drug dosage over time to provide the same level of pain relief to the patient, which in turn may increase the unwanted side effects of the opioid.

A need has arisen for an opioid molecule that delivers effective pain reduction while decreasing or eliminating the undesirable side effects.

SUMMARY OF THE INVENTION

A modified opioid is provided comprising modified morphine molecules, wherein for each morphine molecule, one or more carbon atoms are replaced with silicon atoms.

A modified morphine molecule is further provided having the formula:

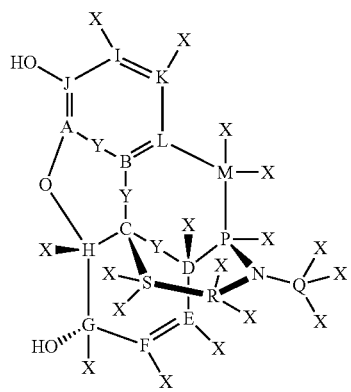

Wherein one or more of A, B, C, D, E, F, G, H, I, J, K, L, M, P, Q, R and S are silicon and the remaining of A, B, C, D, E, F, G, H, I, J, K, L, M, P, Q, R and S are carbon; X is selected from the group consisting of lithium and hydrogen; and Y is selected from the group consisting of a single bond and an oxygen atom.

Further provided is a modified morphine molecule having the formula:

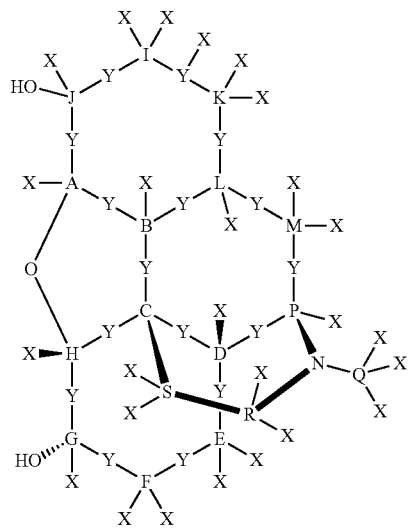

Wherein one or more of A, B, C, D, E, F, G, H, I, J, K, L, M, P, Q, R and S are silicon and the remaining of A, B, C, D, E, F, G, H, I, J, K, L, M, P, Q, R and S are carbon; X is selected from the group consisting of lithium and hydrogen; and Y is selected from the group consisting of a single bond and an oxygen atom.

Finally, a method is provided for modifying an opioid comprising morphine molecules, said method comprising the step of replacing one or more carbon atoms with silicon atoms.

It is to be understood that other aspects of the present invention will become readily apparent to those skilled in the art from the following detailed description, wherein various embodiments of the invention are shown and described by way of illustration. As will be realized, the invention is capable for other and different embodiments and its several details are capable of modification in various other respects, all without departing from the spirit and scope of the present invention. Accordingly the drawings and detailed description are to be regarded as illustrative in nature and not as restrictive.

BRIEF DESCRIPTION OF THE DRAWINGS

A further, detailed description of the invention will follow by reference to the following drawings of specific embodiments of the invention. The drawings depict only typical embodiments of the invention and are therefore not to be considered limiting of its scope. In the drawings.

DESCRIPTION OF THE INVENTION

The description that follows and the embodiments described therein are provided by way of illustration of an example, or examples, of particular embodiments of the principles of various aspects of the present invention. These examples are provided for the purposes of explanation, and not of limitation, of those principles and of the invention in its various aspects.

The invention relates to novel opioid molecules that are similar in molecular structure to morphine, wherein selected carbon atoms in the known opioid molecular structure are substituted for silicon atoms.

Silicon based opioids are understood to synthetically mimic or enhance the functions of morphine. It is known that silicon can mimic the bioactivities of carbon and that carbon has similar valances and similar atomic vibrations to silicon, for example as seen in organosilanes and in silanediol. Silanediol peptic isosters have been used in the past an inhibitors of 4-Hydroxynonenal (HNE) an unsaturated hydroxyalkenal produced by the body. As well, decamethylcyclopenta siloxane (d5) has been seen to have an influence of the neurotransmitter dopamine.

It is also know that silanols can mimic a hydrated carbonyl and inhibit protease enzymes. It is also known that molecules having aromatic rings connected to 3 carbon atoms and a nitrogen atom have shown affinity in binding to opiate receptors.

In morphine, the cationic amine and anionic phenolic hydroxyl group bridge across the opiate receptor site with the alcohol being hydrogen-bonded to the cysteine sulfur. In this way, morphine molecules tend to occupy the space of met encephalin.

It is hypothesized by the inventor that based on the above observances; a synthetic silicon opioid would be able to mimic the naturally occurring opioid.

In a further preferred embodiment of the present invention, select hydrogen atoms in the known opioid molecular structure are substituted for lithium atoms. Lithium can substitute for hydrogen atoms since in many ways, the lithium-silicon bond is similar to a hydrogen-carbon bond.

In some embodiments of the invention, selected bonds between the silicon atoms are substituted with siloxane groups (Si—O—Si). In other embodiments of the invention, the double bonds between carbon atoms in the molecular structure of morphine are substituted with single bonds between silicon atoms. The modified opioid molecules of the present invention containing silicon and optionally also containing lithium, have molecular structures that are similar to the known morphine molecule. It is thus predicted that the silicon opioids will interact with the opioid receptors through similar pharmacokinetic mechanisms as the morphine molecule.

Figure 1A:
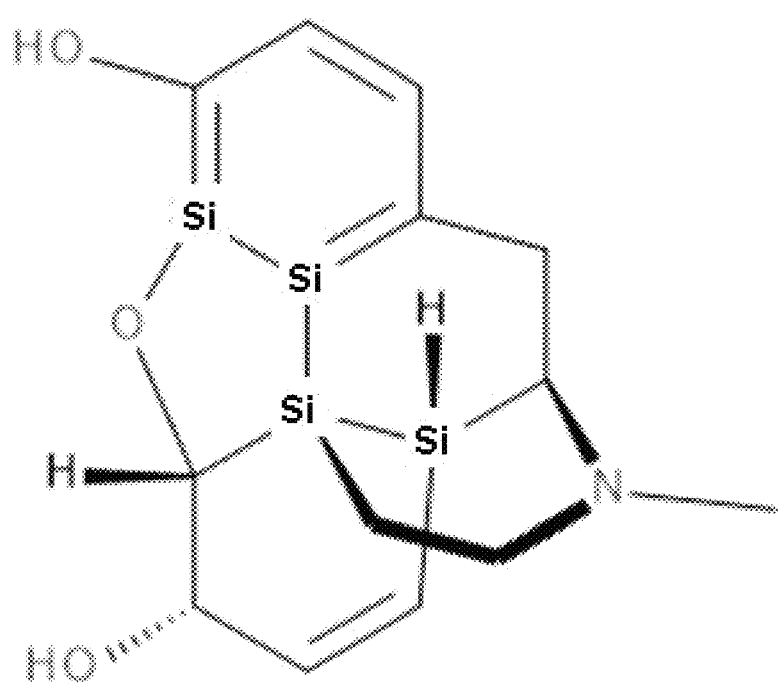
FIG. 1a is an illustration of the molecular structure of a first modified opioid of the present invention.

With reference to the figures, FIG. 1a illustrates a structural analogue of the morphine molecule wherein four selected carbon atoms are substituted with four silicon atoms. This embodiment of the modified opioid is $C_{13}H_{18}NO_3Si_4$.

Figure 1B:
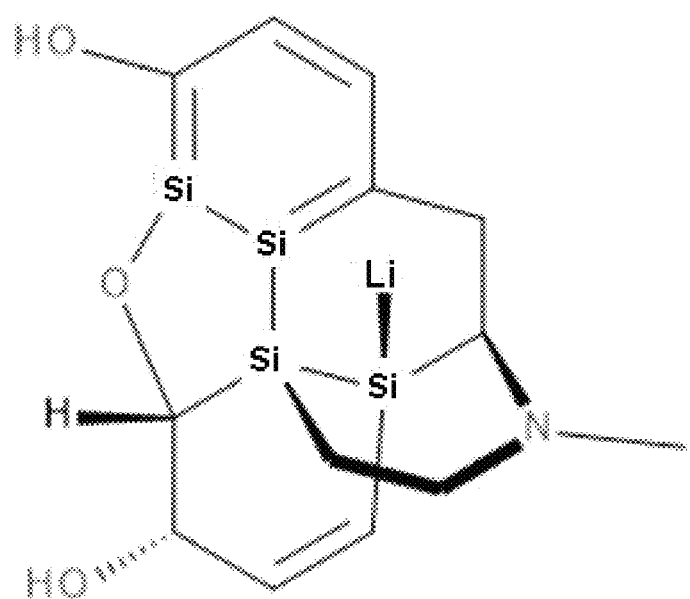
FIG. 1b is an illustration of the molecular structure of a second first modified opioid of the present invention.

FIG. 1b shows a structural analogue of the morphine molecule wherein four selected carbon atoms are substituted with four silicon atoms and one selected hydrogen atom is substituted with one lithium atom. This embodiment of the modified opioid is $C_{13}H_{18}LiNO_3Si_4$.

Figure 2:
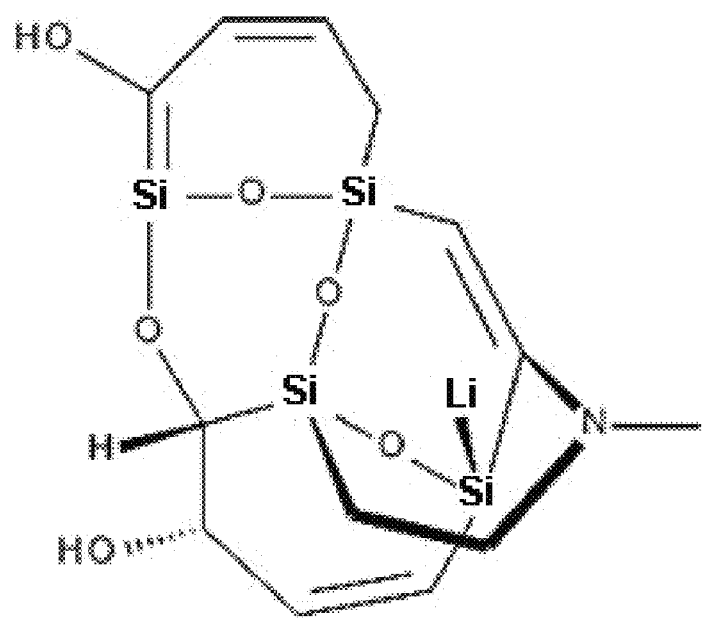
FIG. 2 is an illustration of the molecular structure of a third modified opioid of the present invention.

FIG. 2 illustrates the molecular structure for $C_{13}H_{18}LiNO_6Si_4$, a structural analogue of the morphine molecule wherein three siloxane groups are substituted for the three Si—Si bonds of the molecule illustrated in FIG. 1.

Figure 3:
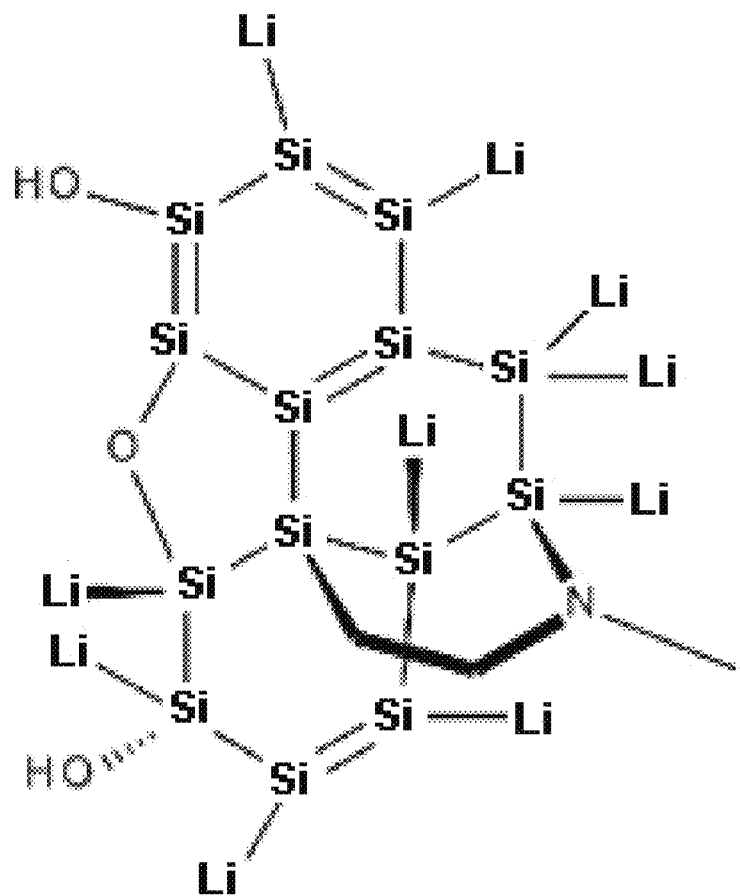
FIG. 3 is an illustration of the molecular structure of a fourth modified opioid of the present invention.

FIG. 3 illustrates the molecular structure for $C_3H_9Li_{10}NO_3Si_{14}$, a structural analogue of the morphine molecule wherein fourteen selected carbon atoms are substituted with fourteen silicon atoms and ten selected hydrogen atom are substituted with ten lithium atoms.

Figure 4:
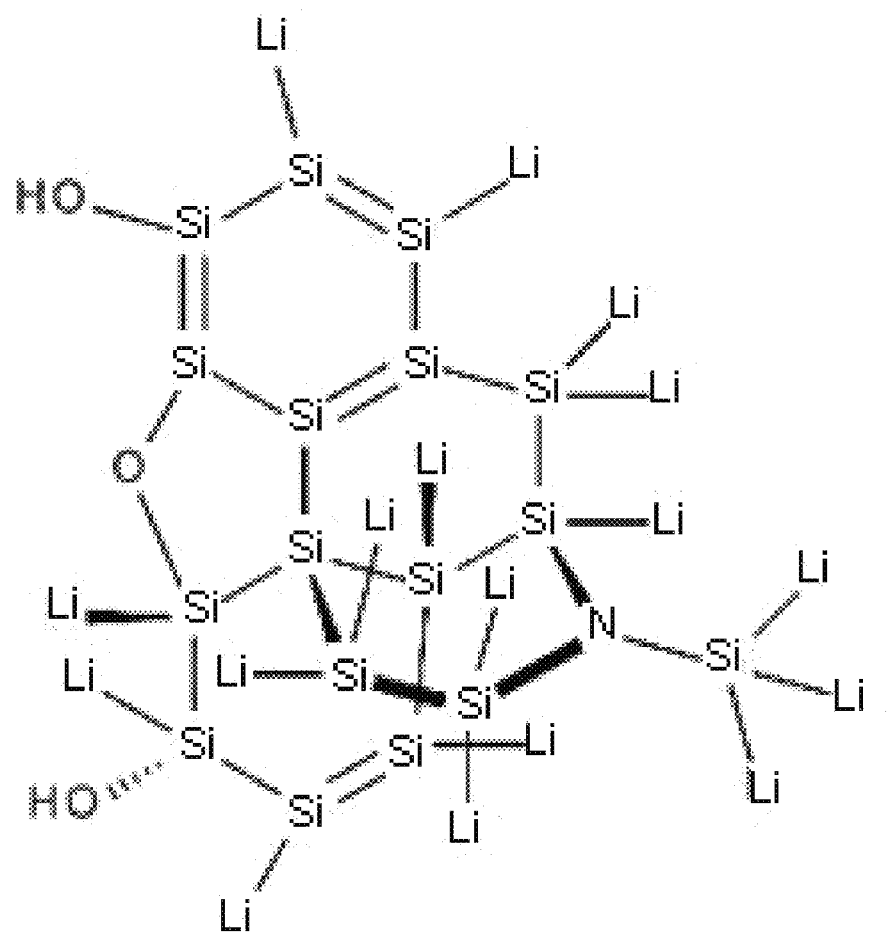
FIG. 4 is an illustration of the molecular structure of a fifth modified opioid of the present invention.

FIG. 4 shows a molecular structure for $H_2Li_{17}NO_3Si_{17}$, a structural analogue of the morphine molecule wherein all seventeen carbon atoms are substituted with seventeen silicon atoms and all of the hydrogen atoms other than the hydrogen atoms on the two hydroxyl groups are substituted with lithium atoms.

Figure 5:
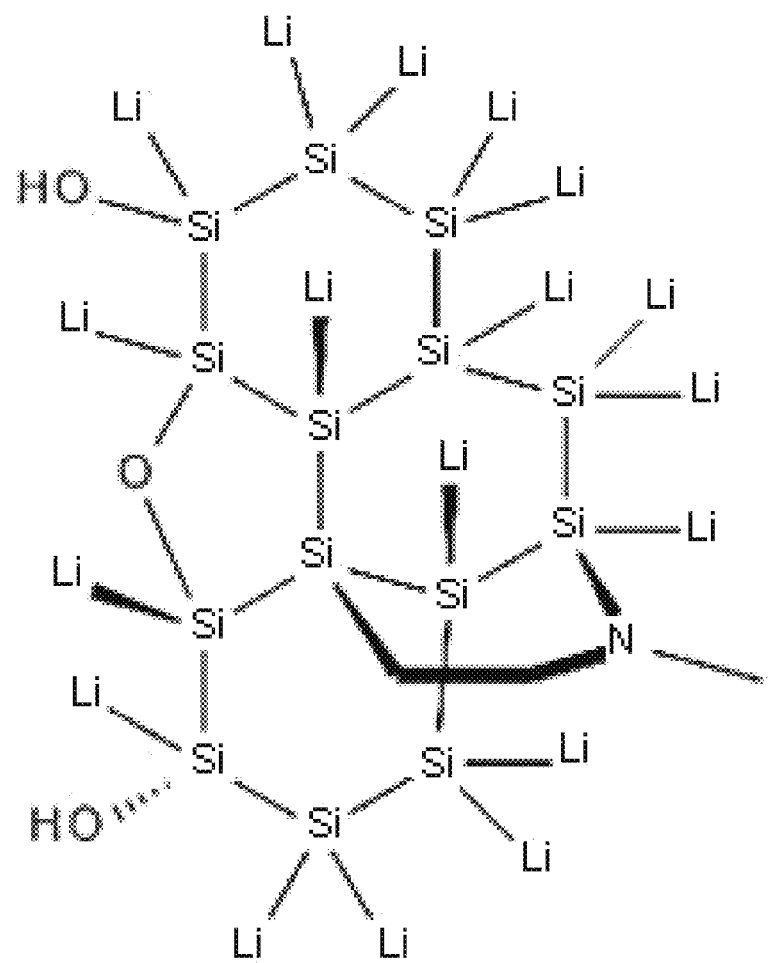
FIG. 5 is an illustration of the molecular structure of a sixth modified opioid of the present invention.

FIG. 5 illustrates a molecular structure for $C_3H_9Li_{18}NO_3Si_{14}$, a structural analogue of the morphine molecule wherein fourteen selected carbon atoms are substituted with fourteen silicon atoms, the four double bonds between silicon atoms are substituted with single bonds, and eighteen selected hydrogen atoms are substituted with eighteen lithium atoms.

Figure 6:
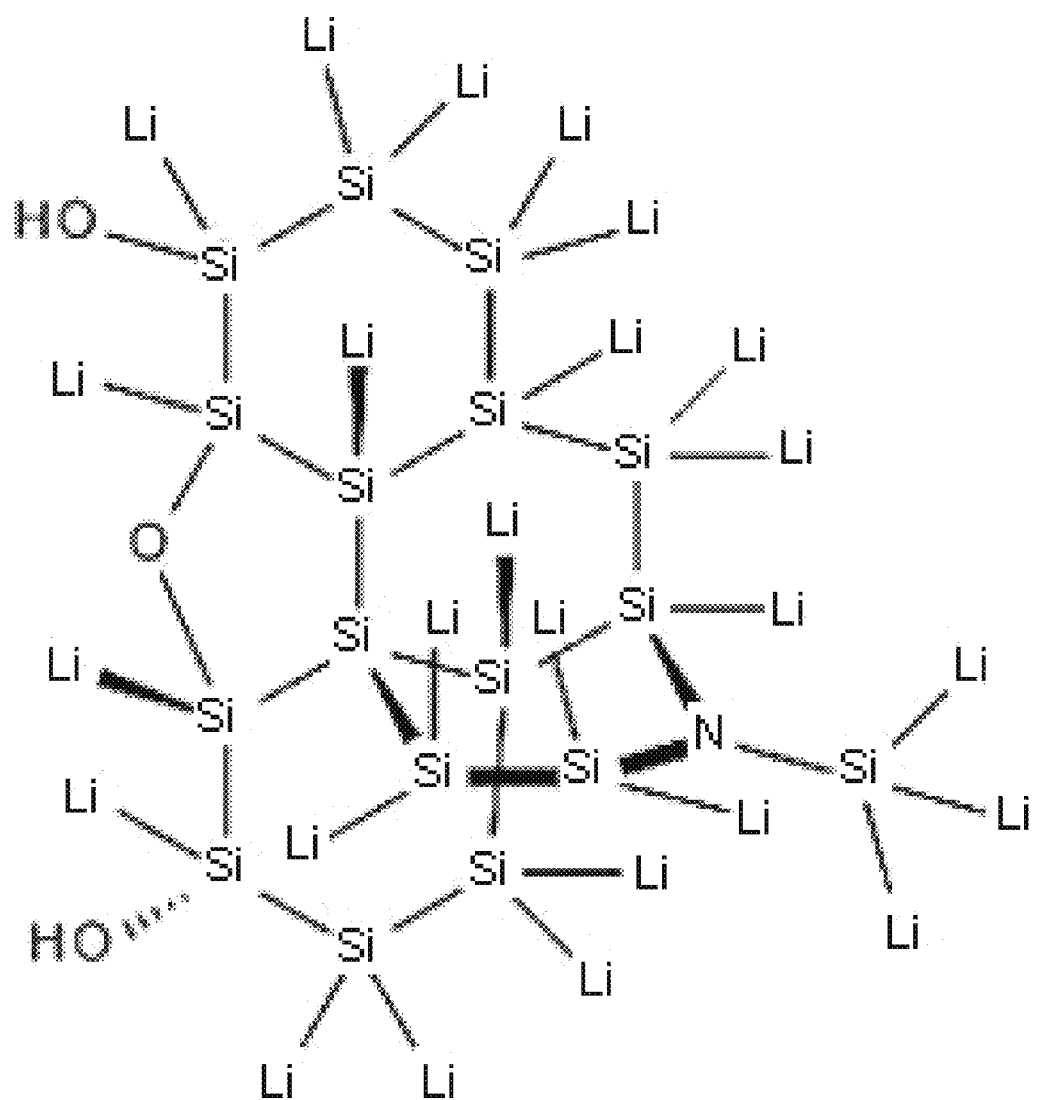
FIG. 6 is an illustration of the molecular structure of a seventh modified opioid of the present invention.

FIG. 6 illustrates a molecular structure for $H_2Li_{25}NO_3Si_{17}$, a structural analogue of the morphine molecule wherein all seventeen carbon atoms are substituted with silicon atoms, the four double bonds between silicon atoms are substituted with single bonds, and all of the hydrogen atoms other than the hydrogen atoms on the two hydroxyl groups are substituted with lithium atoms.

Figure 7:
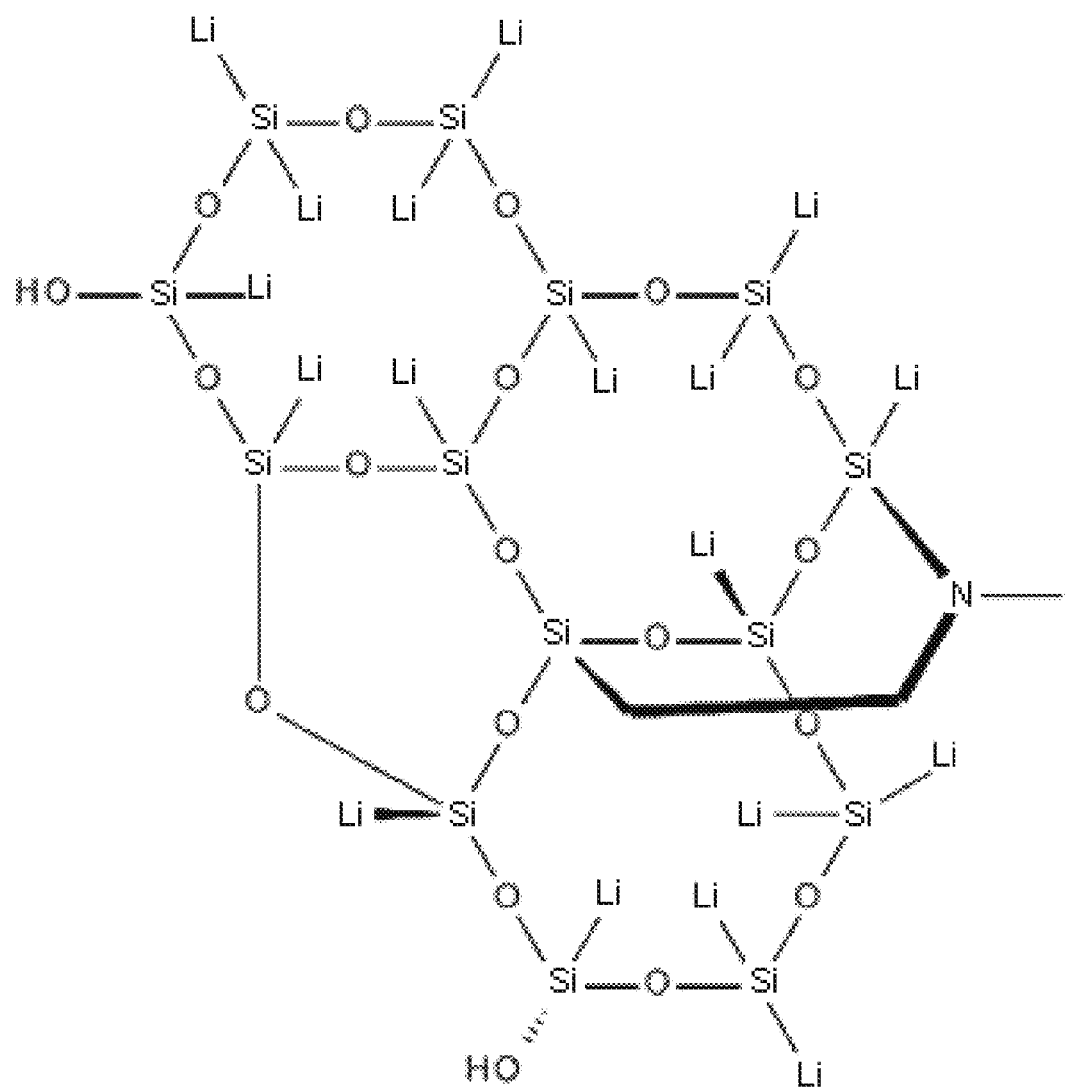
FIG. 7 is an illustration of the molecular structure of a eighth modified opioid of the present invention.

FIG. 7 shows a molecular structure for $C_3H_9Li_{18}NO_{19}Si_{14}$, a structural analogue of the morphine molecule wherein all of the hydrogen atoms bonded to carbon atoms in the morphine molecule are substituted with lithium atoms, fourteen selected carbon atoms are substituted with fourteen silicon atoms and all of the Si—Si bonds are substituted for siloxane groups.

Figure 8:
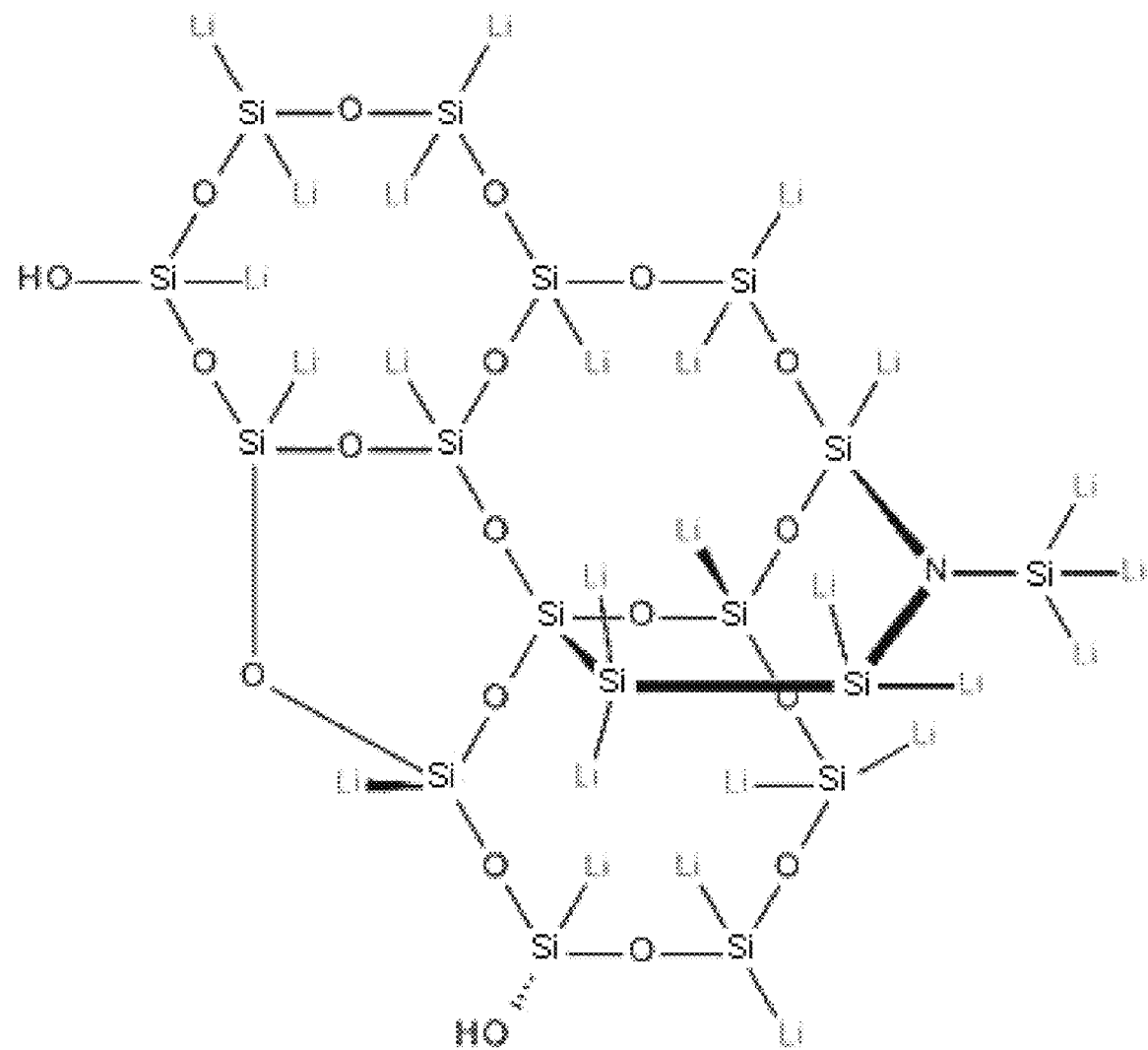
FIG. 8 is an illustration of the molecular structure of a ninth modified opioid of the present invention.

FIG. 8 illustrates a molecular structure for $H_2Li_{25}NO_{19}Si_{17}$, a structural analogue of the morphine molecule wherein all seventeen carbon atoms are substituted with silicon atoms, the four double bonds between silicon atoms are substituted with single bonds, all of the hydrogen atoms other than the hydrogen atoms on the two hydroxyl groups are substituted with lithium atoms and all of the Si—Si bonds are substituted for siloxane groups.

Because the mass of a silicon atom is greater than the mass of a carbon atom, it is predicted that the silicon opioids are more likely to have a stronger attraction to the opioid receptors in the human body. Furthermore, it is hypothesized that silicon-lithium bonds in the modified opioid of the present invention improve the stability of the overall molecular structure.

The silicon containing opioids of the present invention can be synthesized by any number of means that would be known to an ordinary person skill in the art.

As an example, but in no way limiting to the present invention, the silicon containing opioids of the present invention can by synthesized by mechanical means, such as by atomic manipulation. One mechanism using atomic manipulation is scanning tunneling microscope (STM) to manipulate single atoms through controlled, tunable interaction between the atoms at the end of an STM probe tip to create desired nanostructures on a surface that is being manipulated. STM manipulation of atoms may be used to induce disassociation of the carbon atoms from a morphine molecule spine and then bonding of the silicon atoms into the spine.

It is also possible to employ the use of ultra-short laser-pulses to heat and weaken carbon-hydrogen bonds and substitute in silicon or lithium at desired locations.

It is also possible to synthesize the silicon and lithium containing opioids of the present invention by chemical reactions such as by carbolithiation reaction of an organolithium reagent, in which a carbon-lithium bond is added to a carbon-carbon double or triple bond, forming new organolithium species. This can then be followed by a reaction with silanol or organosilicon. A quaternary ammonium cation can then be added to the resultant structure to develop the present silicon and lithium containing opioid shape. In a most preferred embodiment, a pre-synthesized organolithium is reacted with a pre-synthesized siloxane or silanol to form the resultant modified opioid. In a further embodiment, chemical reaction of silicon hydrides having silicon-hydrogen bonds may be implemented in hydrosilylation, a reaction commonly used to create organosilicon compounds.

Another chemical reaction means may use lithium-halogen exchange which could also include reactions of exchange with bromide, that is, a bromine-lithium exchange.

In a further embodiment, metalation, which results in a metal atom being attached to an often organic molecule, can be used. For example, lithium metal in contact with an organohalide tends to lithiate the organic molecule and results in an organolithium reagent and lithium halide.

Figure 9:
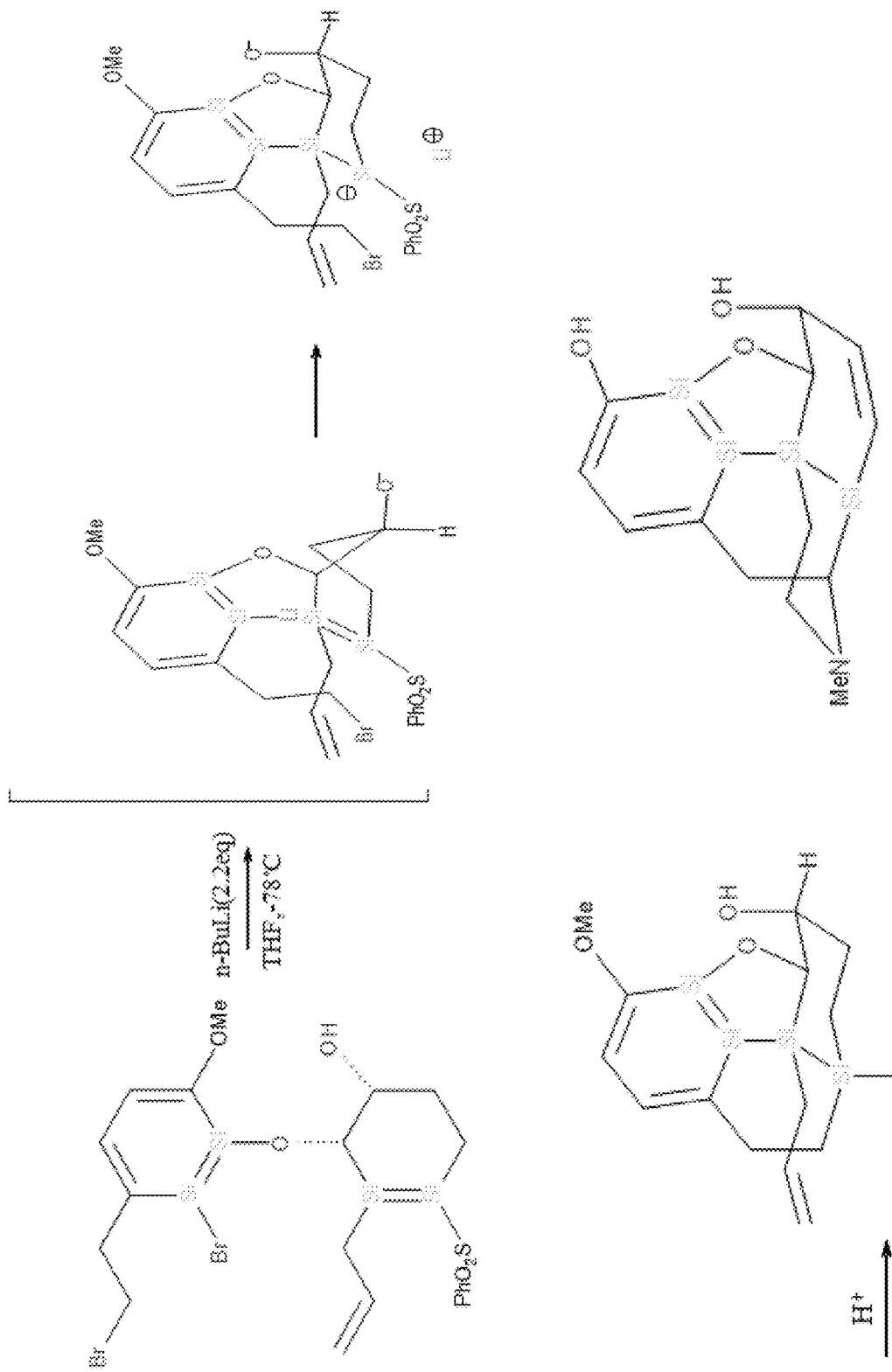
FIG. 9 is an illustration of a first chemical reaction to form the modified opioids of the present invention.

With reference to FIG. 9, this illustrates one example of how a tetracyclic core can be formed using disilabenzene as a substitute for benzene in the beginning stages of synthesis of morphine. The bromine and sulphur dioxide sulphates are then removed to form one of the modified opioids of the present invention. It is further possible to create silicon lithium bonds on the final molecular structure of FIG. 9 by using bromine for a lithium-hydrogen exchange. In this way, it is possible that one or more siloxane strands could be manipulated into hexagonal rings with an oxygen atom binding two organosilicon groups. Then bromine or iodine can be used to manipulate the hexagonal ring structures in to a tetracyclic core of the modified opioid of the present invention.

Figure 10:
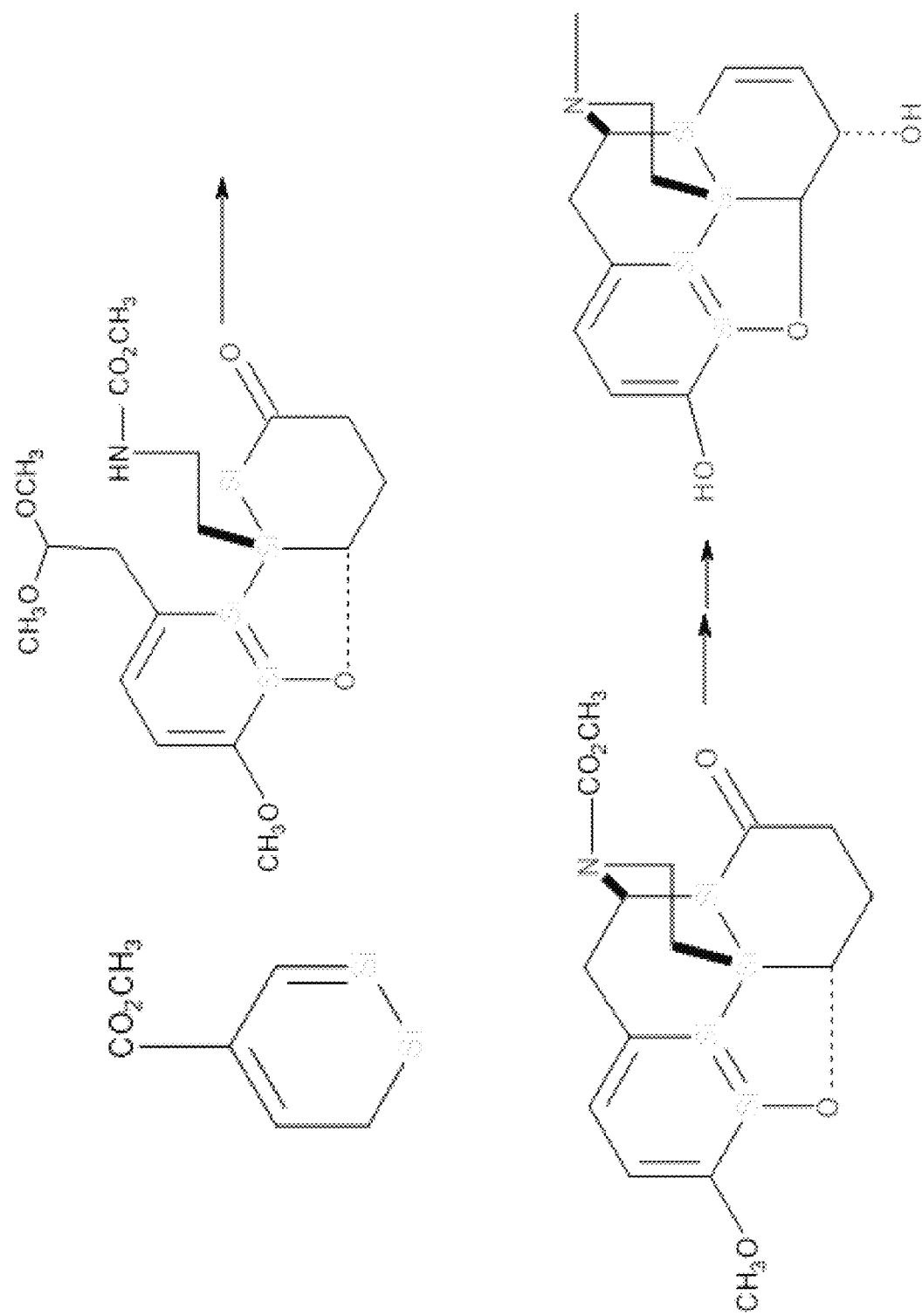
FIG. 10 is an illustration of a second chemical reaction to form the modified opioids of the present invention.

With reference to FIG. 10, is an example of how a disilabenzene ring can replace benzene in the beginning stages of a Fukuyama total synthesis of morphine:

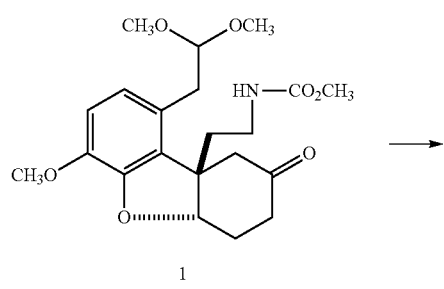

1

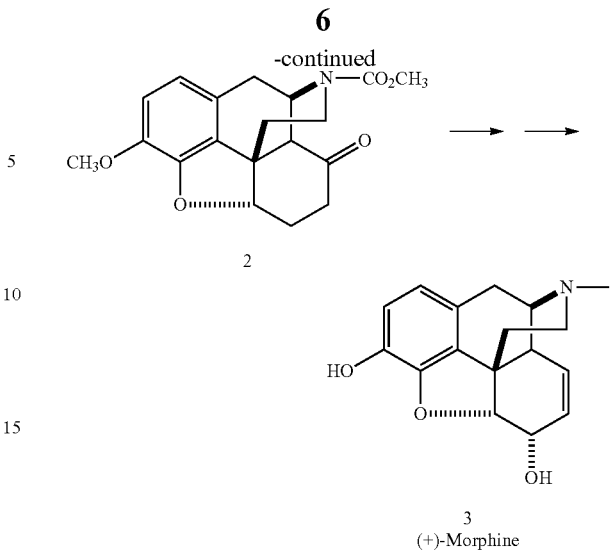

2

3
(+)-Morphine from where the Fukuyama synthesis can be applied with a disilabenzene inner core. Furthermore, it is hypothesized that a hexasilane, a disilane or a trisilane may be attached to a siloxane strand. Then bromine or iodine can be used to manipulate the hexagonal ring structures in to a tetracyclic core of the modified opioid of the present invention.

In the embodiments above including siloxane groups, it is predicted that siloxane groups may be an effective means of counteracting the possible immunogenicity of the molecule, potentially resulting in the reduction of some undesirable side effects caused by known opioid molecules, including nausea and vomiting. Additionally, is hypothesized that silicon opioids may metabolize in the human body at an increased rate relative to the rate at which the corresponding carbon-containing opioid molecules metabolize in the human body, due to the increased size of a silicon atom relative to a carbon atom. This may result in a relatively lower dosage of the silicon-containing opioid molecules to achieve the desired analgesic effect.

The previous description of the disclosed embodiments is provided to enable any person skilled in the art to make or use the present invention. Various modifications to those embodiments will be readily apparent to those skilled in the art, and the generic principles defined herein may be applied to other embodiments without departing from the spirit or scope of the invention. Thus, the present invention is not intended to be limited to the embodiments shown herein, but is to be accorded the full scope consistent with the claims, wherein reference to an element in the singular, such as by use of the article "a" or "an" is not intended to mean "one and only one" unless specifically so stated, but rather "one or more". All structural and functional equivalents to the elements of the various embodiments described throughout the disclosure that are known or later come to be known to those of ordinary skill in the art are intended to be encompassed by the elements of the claims.

The invention claimed is:

1. A modified opioid comprising modified morphine molecules, wherein the modified morphine molecules are selected from a group comprising:

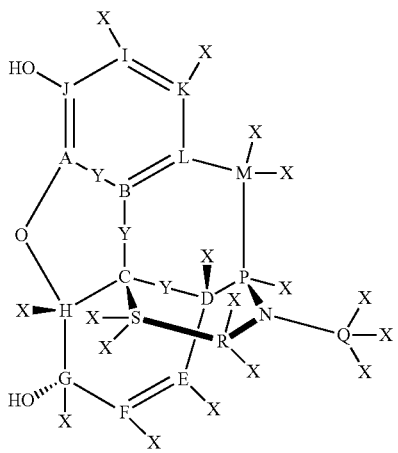

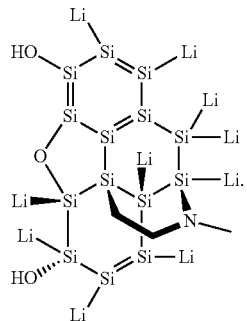

4. The modified opioid of claim 1, wherein the modified morphine molecule is:

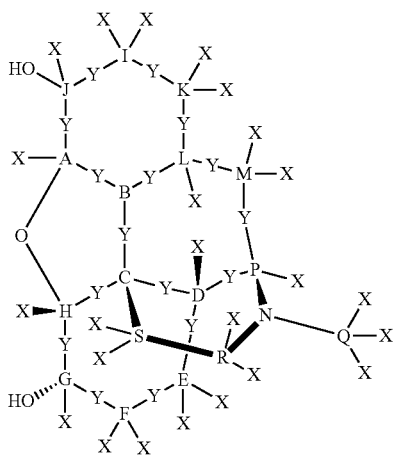

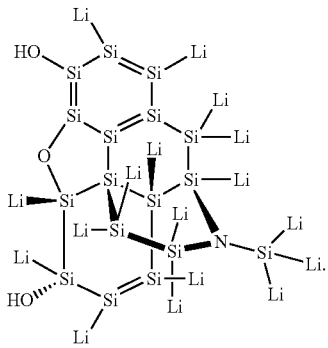

wherein:
one or more of A, B, C, D, E, F, G, H, I, J, K, L, M, P, Q, R and S are silicon and the remaining of A, B, C, D, E, F, G, H, I, J, K, L, M, P, Q, R and S are carbon;
X is selected from the group consisting of lithium and hydrogen; and
Y is selected from the group consisting of a single bond and an oxygen atom.

2. The modified opioid of claim 1, wherein the modified morphine molecule is:

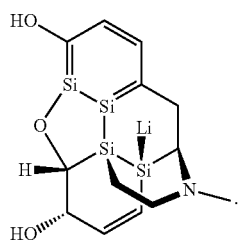

3. The modified opioid of claim 1, wherein the modified morphine molecule is:

5. The modified opioid of claim 1, wherein the modified morphine molecule is:

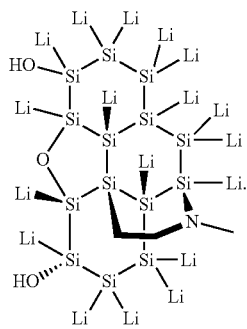

6. The modified opioid of claim 1, wherein the modified morphine molecule is:

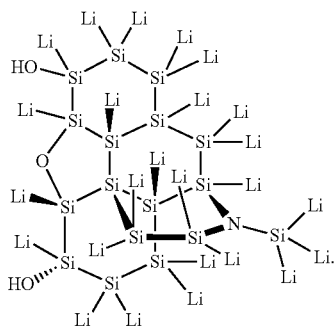

7. The modified opioid of claim 1, wherein the modified morphine molecule is:

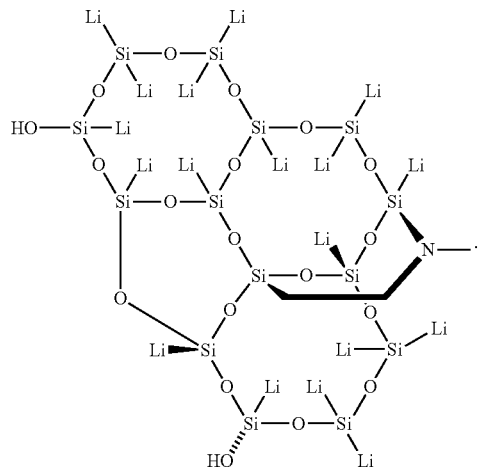

8. The modified opioid of claim 1, wherein the modified morphine molecule is:

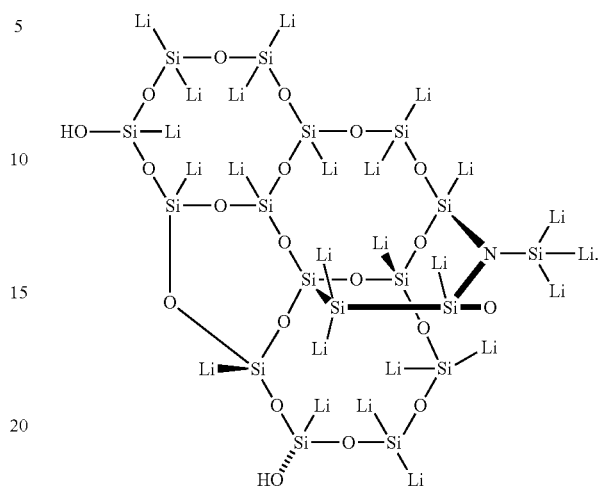

9. A method of modifying the modified morphine molecules of claim 1, said method comprising the step of replacing one or more carbon atoms with silicon atoms.

10. The method of claim 9, further comprising replacing one or more hydrogen atoms with lithium atoms.

11. The method of claim 9, further comprising replacing one or more silicon-silicon single bonds with siloxane groups.

12. The method of claim 10, further comprising replacing one or more silicon-silicon double bonds with a silicon-silicon single bond and a silicon-lithium single bond.

13. The method of claim 12, further comprising replacing one or more silicon-silicon single bonds with siloxane groups.

* * * * *